United States Patent
Schelkle

(10) Patent No.: US 9,572,850 B2
(45) Date of Patent: Feb. 21, 2017

(54) **USE OF CAJEPUT AND *PIMENTA RACEMOSA* EXTRACT FOR TREATING PARASITIC INFESTATION OF FISH**

(75) Inventor: Bettina Schelkle, Cardiff (GB)

(73) Assignee: Mars, Incorporated, McLean, VA (US)

( * ) Notice: Subject to any disclaimer, the term of this patent is extended or adjusted under 35 U.S.C. 154(b) by 717 days.

(21) Appl. No.: 13/390,096

(22) PCT Filed: Aug. 9, 2010

(86) PCT No.: PCT/EP2010/061543
§ 371 (c)(1),
(2), (4) Date: Apr. 18, 2012

(87) PCT Pub. No.: WO2011/015668
PCT Pub. Date: Feb. 10, 2011

(65) Prior Publication Data
US 2012/0276227 A1   Nov. 1, 2012

(30) Foreign Application Priority Data
Aug. 7, 2009   (GB) .................................. 0913968.4

(51) Int. Cl.
*A61K 36/00* (2006.01)
*A61K 36/61* (2006.01)

(52) U.S. Cl.
CPC ............... *A61K 36/61* (2013.01); *A23K 50/80* (2016.05)

(58) Field of Classification Search
None
See application file for complete search history.

(56) References Cited

U.S. PATENT DOCUMENTS

| 5,882,647 | A | 3/1999 | Yoshpa |
| 6,537,591 | B2 | 3/2003 | Yoshpa |
| 2007/0237837 | A1* | 10/2007 | Pipko ..................... A61K 31/19 424/717 |
| 2008/0026083 | A1 | 1/2008 | Reynolds |

FOREIGN PATENT DOCUMENTS

| JP | 2001069922 | 3/2001 |
| JP | 2006306777 | 11/2006 |

OTHER PUBLICATIONS http://web.archive.org/web/20060523093613/http://www.drsfostersmith.com/product/add_info.cfm?pCatId=11269.
Wayback Machine: Doctor Foster and Smith; "PimaFix & MelaFix" May 23, 2006. Downloaded from www on Feb. 7, 2013.*
CHEMWATCH-MELA-FIX-19-NOV2009. Downloaded from www on Feb. 11, 2013.*
Steverding, et al., "Effect of Australian tea tree oil on *Gyrodactylus* spp. infection on the three-spined stickelback Gasterosteus aculateus", Diseases of Aquatic Organisms, vol. 66, No. 1, Aug. 9, 2005, 29-32.
Scholz, "Parasites in Cultured and Feral Fish", Veterinary Parasitology, (1999), 84:317-335.

* cited by examiner

*Primary Examiner* — Qiuwen Mi
(74) *Attorney, Agent, or Firm* — Mars, Incorporated; Colleen Kramer

(57) ABSTRACT

The present invention relates to a combination of cajeput and extract from the plant *Pimenta racemosa* for use in preventing ornamental fish parasite infestation or removing ornamental fish parasites. The combination of cajeput and extract from the plant *Pimenta racemosa* is administered to the fish.

21 Claims, 1 Drawing Sheet

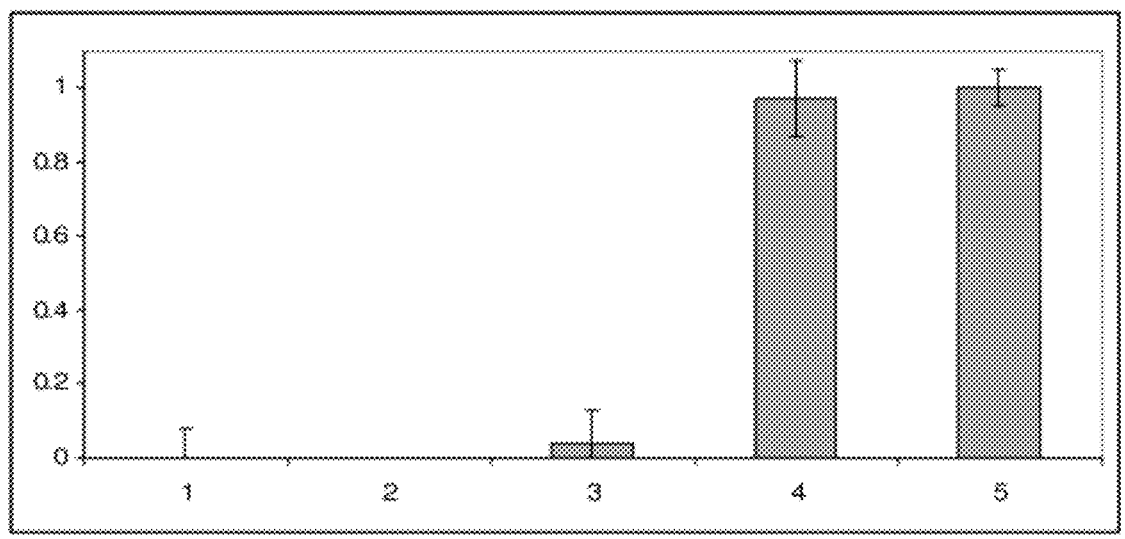

USE OF CAJEPUT AND *PIMENTA RACEMOSA* EXTRACT FOR TREATING PARASITIC INFESTATION OF FISH

RELATED APPLICATIONS

This application is a national phase application under 35 USC §371 of PCT Application No. PCT/EP2010/061543, which the claims the benefit of foreign priority to Great Britain Patent Application No. GB 0913968.4, filed Aug. 7, 2009, the teaching and contents of which are hereby incorporated by reference.

The present invention relates to a combination of cajeput and extract from the plant *Pimenta racemosa* for use in preventing ornamental fish parasite infestation or removing ornamental fish parasites. The combination of cajeput and extract from the plant *Pimenta racemosa* is administered to the fish.

Fish parasites in aquaculture are a serious problem as they occur on nearly all fish species reared in confined conditions. Many of these diseases are not easily treated leading to huge economic losses. Amongst these parasites, gyrodactylids are widely distributed. Conventional treatments against gyrodactylidosis include chemicals, such as formalin and malachite green. However, most of these are (1) only partially efficient; (2) toxic to host, environment and/or humans; (3) no longer effective due to resistance; and (4) difficult to apply on a large scale.

In the ornamental fish industry gyrodactylids can cause 90% mortalities and in the food fish industry parasitic diseases can be responsible for economically important outbreaks of disease, so contributing to huge economic losses. This is a result of a combination of factors: (1) the confined conditions of fish farms or aquaria where transmission rates of gyrodactylids between individual fish are high and fish are more susceptible to pathogens due to the stressful environment; (2) the lack of a specific transmission stage during the gyrodactylid life cycle; and (3) the short generation turn over (>24 h at 25° C. in some species). Additionally, gyrodactylids are thought to reproduce parthenogenetically, asexually or sexually during their life cycle which allows them to increase population sizes from single individuals to epidemic populations rapidly. As a result there is great interest in the treatment of these pathogens.

Numerous compounds have previously been used to treat gyrodactylid infections in research facilities, aquaculture and the hobbyist market. However, selecting the best of these treatments is difficult, because few studies have compared compounds using the same methodologies and the majority of treatments have various associated problems. Formaldehyde, for instance, was found to be 100% effective at eliminating *G. salaris* experimentally, but under field conditions it does not eradicate gyrodactylids completely. Furthermore, in some three spined stickleback (*Gasterosteus aculeatus*) populations this treatment is only 10% effective. Due to its broad anti-parasitic properties formaldehyde is still commonly used in aquaculture, even though it is classed as a human carcinogen. Mutagenic and carcinogenic effects are also known for malachite green which like formaldehyde is widely used as an anti-parasitic treatment, but its effectiveness against *Gyrodactylus* spp. has not been evaluated. Malachite green is now banned in food fish production in Europe (European Council Regulation 2377/90) and North America (U.S. Food and Drug Administration and the Canadian Food Inspection Agency) as it is retained in fish flesh. Potential negative effects to human health are known for rotenone, an indiscriminate ATPase inhibitor, which has been used to control *G. salaris* in Norway by killing all potential hosts. This was only partially effective and alternatives such as aqueous aluminium are being tested. However, although aluminium appeared promising in laboratory studies, field trials in Norway have been problematic because successful treatment of the whole river system requires maintaining a specific concentration without exceeding levels toxic to Atlantic salmon.

In addition to the efficacy and human health issues, the main problem associated with current gyrodactylid treatments is their toxicity to the host. Even widely used compounds, such as formaldehyde, may significantly change the host's gill structure and epidermis. For instance, although zinc exposure initially stimulates host mucus production, it then becomes depleted leaving the fish more susceptible to microbial infections. If these fish are subsequently used for experimental infections without a sufficient recovery period, they may show an abnormal response to infection. Host respiratory problems are also a common side effect of gyrodactylid treatments due to direct interference with gill function and indirectly via reduction of water quality. Toxicity in many cases is dose dependent, but may also be affected by one or a combination of the following factors: temperature, pH, salinity, mechanism of delivery, species and exposure time, especially where multiple treatments are used.

Gyrodactylid treatments are applied either orally (with food) or topically (added to the water). Both methods usually lead to application of overly high doses to compensate for lack of control over drug administration (Scholz 1999), which leads to environmental contamination. Oral administration of some drugs can also reduce host food consumption (e.g. piperazine, Fugotenil® and Neguvon®) which increases the dosage needed per unit of food for efficacy. Additionally, compounds that are partially effective as baths may not be effective if administered orally (e.g. trichlorfon). Moreover, increasing resistance of parasites against antihelminthics is reported, with resistance of gyrodactylids to organophosphate dimethyl phosphonate and trichlorfon, respectively.

High and consistent efficacy in treatment of fish parasites is needed, otherwise the remaining parasites multiply and the problem continues.

For small fish (such as poeciliids), manual removal of parasites can be effective without any chemical intervention. However, for larger fish, chemical treatment prior to screening may be the only practical solution to manual parasite removal.

Accordingly, it is desired to overcome the known problems in the art to prevent and/or treat parasites on fish.

A first aspect of the present invention relates to a combination of cajeput and extract from the plant *Pimenta racemosa* for use in preventing ornamental fish parasite infestation or removing ornamental fish parasites.

Cajeput and extract from the plant *Pimenta racemosa* are known. Extract from the plant *Pimenta racemosa* is known.

The active ingredient of *Pimenta racemosa* is an extract from the plants of the genus *Pimenta* and, more particularly, bay. As used herein, the term "*Pimenta racemosa* extract" means extracts of the genus *Pimenta* and the species *Pimenta racemosa*. "*Pimenta racemosa* extract" is used to refer broadly to the active ingredient of the composition and method of the present invention.

As used herein, "bay," sometimes called West Indian bay oil, or *Myrcia*, or bay rum tree oil, is the substance that is obtainable from the tree *Pimenta racemosa* (Mill.) J. W. Moore (syn. *P. acris* Kostel) (Family Myrtaceae), which is indigenous to the West Indies, and is cultivated in Venezuela, Puerto Rico and the Caribbean Islands. Bay contains a large number of components, most of which are terpenoids, and major components being eugenol (up to about 56%), chavicol (up to about 22%) and myrcene (up to about 21%). Other components in lesser amounts include 1,8-cineole, limonene, isoeugenol, linalool, methyl eugenol (3,4-dimethoxyallylbenzene), estragole (methyl chavicol) and α-terpineol.

There are several varieties of bay, including anise-scented, lemon-scented and clove-scented varieties. The distinctions among the varieties include different proportions of the components noted above, for example, the anise-scented variety contains methyl eugenol (about 43%) and methyl chavicol (about 32%) as the major components, and the lemon-scented variety contains mostly citral (greater than about 80%).

Although the commonly used domestic spice is sometimes also referred to as "bay" in the literature, this spice is sweet bay (*Laurus nobilis*), and not West Indian bay used in the present invention.

It is important to note that the active ingredient utilized in this invention is a complex mixture of components normally and naturally found in extracts of the species *Pimenta racemosa* of the *Pimenta* genus, West Indian bay oil, rather than a single component fractionally distilled and separated from such sources, e.g., eugenol. West Indian bay oil is produced in commercial quantities in Venezuela, Puerto Rico, and the Caribbean Islands. The *Pimenta* extract used in the present invention is readily available from commercial suppliers of naturally derived food and cosmetic oils and extracts. The *Pimenta* extract of the present invention is typically produced by the known technique of hydrodistillation (steam distillation) of fresh leaves and twigs of plants of *Pimenta racemosa*.

Bay in its commercially available forms are presently preferred, but other forms of *Pimenta* extract may also be used, e.g., *Pimenta extract* in a liquid (solvent or another oil), *Pimenta* extract in an aqueous mixture, *Pimenta* extract in an aqueous emulsion, *Pimenta* extract adsorbed onto or absorbed into a solid carrier or substrate or *Pimenta* extract associated with other vehicles, provided that such vehicles are compatible with the administration of the *Pimenta* extract into water harboring the aquatic animal to be treated, and do not adversely affect the aquatic animal being treated or other beneficial aquatic life present in the water.

Cajeput or cajeput oil (CAS: 8008-98-8) is known. It is obtainable from leaves of the tree *Melaleuca cajeput, Melaleuca leucardendron* and other species of *Melaleuca* (Myrtaceae). Cajeput oil contains a large number of components, most of which are terpeniods and one major component being 1,8-cineole (about 30%). In the present invention, cajeput is preferably cajeput oil. Cajeput oil is commonly produced by the known technique of hydrodistillation (steam distillation) of fresh leaves and twigs of the *Melaleuca* species. The cajeput of this invention is a complex mixture of components found in cajeput oil and not a single component fractionally distilled and separated from other components. Cajeput oil is produced in commercial qualities in Southeast Asia and is readily available from commercial suppliers of naturally derived food, cosmetic oils and extracts.

Cajeput oil is preferred in view of its commercial availability. Other forms of cajeput may also be used (e.g. a non-oil extract or cajeput absorbed onto or absorbed into solid carrier or substrate).

Cajeput and *Pimenta* racemosa extract can be introduced directly into water containing fish. However, both are relatively insoluble in water and thus it is preferable to use an aqueous mixture or dispersion of both oils unless high speed or high sheer mixing is used (usually in a localized region in the absence of the aquatic animal being treated to avoid injury).

The aqueous cajeput-containing and/or *Pimenta racemosa* extract-containing composition preferably contains an emulsifier in an amount sufficient to emulsify the components in water, to provide a relatively stable emulsion. Preferred emulsifiers (sometimes called surfactants) are those which are nontoxic and noninjurious to the aquatic animal being treated. These include food grade emulsifiers which are widely available.

Nonionic emulsifiers are especially preferred, with Crovol™ PK-70 nonionic emulsifier (Croda Inc., Parsippany, N.J., U.S.A.) being a highly preferred nonionic emulsifier that is water soluble.

The amount of emulsifier used to provide emulsification of the cajeput and/or *Pimenta racemosa* extract in water is generally not critical. The concentration of emulsifier may range from about 0.01% to about 20%, more preferably about 0.1% to about 5%, all percentages being by volume. For emulsifiers or surfactants that are normally not liquid, the numerical concentration ranges just noted may be used, with percentages being by weight based on the volume of aqueous emulsion.

Other adjuvants besides emulsifiers may also be used, such as antifoams or defoamers, antioxidants, preservatives, coloring agents and the like. The adjuvants are typically present in the aqueous cajeput-containing and/or *Pimenta racemosa*-containing composition in minor amounts, i.e., less than about 5% by volume and preferably less than 1% by volume. All such adjuvants should be noninjurious and nontoxic to the fish and other aquatic animals being treated, as well as to other beneficial aquatic organisms present in the water along with the aquatic animal being treated, such as various types of invertebrates and plants.

A particularly preferred stable emulsified aqueous composition is as follows:

| | |
|---|---|
| cajeput and/or *Pimenta racemosa* extract | 1% by volume |
| emulsifier | 1% by volume |
| defoamer | 0.2% by volume |
| deionized water | 97.8% by volume |

The emulsifier is preferably Crovol™ PK-70 nonionic emulsifier (Croda Inc.) and the defoamer is preferably FG-10 antifoam (Dow-Corning Corp., Midland, Mich., U.S.A.), the latter serving to control foaming otherwise caused by the emulsifier. The composition may be prepared by vigorously mixing the cajeput and/or *Pimenta racemosa* extract, emulsifier and defoamer in the deionized water, to produce an aqueous emulsion that is stabilized against separation of the cajeput oil from the aqueous phase. Such mixing may be carried out with a mechanical mixer or by manual shaking.

An aqueous mixture containing cajeput and/or *Pimenta racemosa* extract, e.g., 1% by volume, can be prepared without the emulsifier and defoamer, but such an aqueous mixture must be vigorously shaken (for 1-5 minutes) or mechanically agitated prior to use to disperse the cajeput oil uniformly throughout the aqueous phase.

Emulsified cajeput is sold as an oil with 1% active ingredient from Aquarium Pharmaceuticals (as MelaFix®)

Preferably, any aqueous mixture or dispersion of cajeput or extract from *Pimenta racemosa* is added to water containing (or to contain) fish in a manner that ensures further mixing of the mixture or dispersion in the water. This can be by aeration of the water by filter pump or aerator or by a gentle mixing of the water after the cajeput or extract of *Pimenta racemosa* is added. Alternatively, vigorous shaking of the cajeput, or extract of *Pimenta racemosa* (in any form) and optionally with water can be beneficial before adding to the fish habitat. The vigorous shaking may be with some or all of the water which provides the water for the fish to inhabit.

Oil from the plant *Pimenta racemosa* is known as bay oil (CAS: 8006-78-8) and is also sold as an oil with 1% active ingredient from Aquarium Pharmaceuticals (as Pimafix®).

Preferably the cajeput oil is from the species *Melaleuca leucadendra*.

Cajeput and *Pimenta racemosa* extract are known and are known for inclusion in fish habitats (see WO98/00025 and WO02/069989, respectively, the content of each of which is incorporated by reference in its entirety). However, it is novel and surprisingly beneficial to combine these ingredients to treat or prevent parasite (infections/infestations) on fish.

The present invention relates to preventing ornamental fish parasite infestation or removing ornamental fish parasites. Ornamental fish are herein defined as fish kept in the aquarium hobby and pond fish (i.e. fish kept as a hobby), but does not include fish kept for food or sport.

In accordance with the invention, the cajeput and *Pimenta racemosa* extract are for simultaneous, subsequent or sequential administration. The cajeput and *Pimenta racemosa* extract can be added in any order. The cajeput and the *Pimenta racemosa* extract may be added separately or together (i.e. from separate or the same containers). The two active agents may be in the form of a kit, where they are retained in separate containers which are physically linked (a single unit divided into two containers or two containers in a single pouch or box), with instructions for use.

In accordance with the invention, the use of the cajeput and *Pimenta racemosa* extract may be for addition to a fish habitat prior to populating the habitat with fish. The cajeput and *Pimenta racemosa* extract (each or both) may be added before the water, with the water or after the water.

Each of the cajeput and *Pimenta racemosa* extracts is preferably present in the range of from 0.1-15%, preferably 0.5-3% more preferably 0.8 to 1.5%, most preferably about 1% of the product (before adding to the water in which the fish are/will be present). The combined active ingredients are preferably present in the water in which the fish are found or to be found in the range of from about 0.001 ml to about 1 ml per day per 10 gallons (approximately 38 liters) or from 0.4 to 3 ml/380 liters, more preferably from 0.8 to 2 ml/380 liters, most preferably about 1 ml/380 liters. These amounts may be added daily to water. The combined actives are preferably used in ratio of approximately 1:1 with some variability of up to 50% either way.

The cajeput and the *Pimenta racemosa* extract can be used for any period of time and can be used continually. They may particularly be used for a period of from 3 to 9 days for the treatment of parasites on fish. Each of the cajeput and the *Pimenta racemosa* extract may be added at any frequency to the fish habitat, for example once daily.

The parasite may be any that appear on the external surface of the fish (skin, fins and gilss) and are classed as ecto-parasites. Parasites prevented and treated according to the present invention include monogenean parasites, such as skin flukes *Gyrodactylus* spp and gill flukes *Dactylogyrus* spp, protozoan parasites such as *Ichthyophthirius multifiliis*, *Trichodina*, *Ichthyobodo* (Costia), *Chilodonella* and *Pleistophora*, the dinoflagellate *Picinoodinium* (Oodinium), the aquatic crustacean parasites *lernea* (anchor worm) and *Argulus*, the larval stages of digenean parasites *Clinostomum*, *Posthodiplostomum* and *Diplostomum* and endoparasites worms (including cestodes and meatodes) including *Spironucleus* and *Hexamita*.

Particular ornamental fish to which the invention relates, include guppies (*Poecilia reticulata*), all other live bearing species (Cyprinodontiformes, i.e swordtails, platys and mollies) and the following classification orders; Cypriniformes (i.e. goldfish, carp, danios), Characiformes (i.e. tetras, hatchet fish), Siluriformes (catfish), Antheriniformes (rainbowfish), and Perciformes (i.e. gourami, bettas, cichlidsm discus, angelfish, clownfish). This invention also relates to all ornamental fish that can be held in outdoor 'garden' ponds, i.e. carp (i.e. koi, mirror, grass), orfe and tench.

A second aspect of the present invention relates to a method of preventing ornamental fish parasite infestation or removing ornamental fish parasites by administering a combination of cajeput and *Pimenta racemosa* extract to the fish.

The present invention relates to both prophylactic and therapeutic use of cajeput and *Pimenta racemosa* extract. Thus, fish to be transported in shipping containers may be treated beforehand or during shipping to reduce the presence of fish parasites. One fish habits according to the present invention include a holding tank, aquarium, pool, small pond or fish tank.

All preferred features of the first aspect also apply to the second.

The present invention is described with reference to the following non-limiting example:

EXAMPLE

Herbal Treatments

Material and Methods
Source of Animals and Compounds

Guppies (*P. reticulata*) were obtained from Cardiff University's inbred ornamental stock. They were fed on a mixture of live food (*Daphnia* and *Artemia* spp.) and Aquarian fish flakes at least twice daily and were maintained at 25±1° C. with a 12 h dark:12 h light cycle. The Gt3 strain of *G. turnbulli* maintained in the laboratories was used, which was isolated from a pet shop guppy in Nottingham in 1997. Five compounds were tested: 0.5 mg/l allyl disulphide (Sigma Aldrich, cat. no. W202800); 132 µl/l Melafix® and Pimafix® (marketed by API Aquarium Pharmaceuticals and used according to manufacturer's instructions); 0.15 mg/l levamisole (Levacide® acquired from Norbrook®) and 132 µl/l Polyaqua® (Kordon®).
Experimental Trials In all experimental trials we included mortality controls (uninfected fish) which did not receive treatment, as did the infected controls. On D1 (day 1) and D8 (day 8) the number of parasites and their location on the host were recorded by screening fish anaesthetised with 0.02% MS222 using a stereo-microscope and cold light illumination.

In the first trial, 134 fish with naturally acquired multi-parasite infections, purchased from a commercial supplier, were kept individually in 11 containers and treated with either Melafix®, Pimafix®, Melafix®/Pimafix® or Polyaqua® after daily water changes over a period of 7 d. In a second trial, single guppies (n=115) each infected with 2-200 *G. turnbulli* were maintained as in Trial 1 and received treatments of either allyl disulphide, Pimafix®, Melafix® or a Pimafix®/Melafix® combination.

In a third trial, juvenile guppies (n=30) each infected with 10-40 individuals of *G. turnbulli* were maintained together in shoals of 3 fish in 5l aquaria with an air supply, but no tank ornamentation, and treated with allyl disulphide, levamisole, Melafix® and/or Pimafix®. All treatments were applied daily for 7 days. As levamisole is less bio-degradable than all other compounds, a second levamisole treatment received daily water changes to avoid rising concentrations of levamisole throughout the experimental period.

Fate of Animals

At the end of the experimental trials, fish that were still infected with parasites received a levamisole treatment. All fish were then retained in individual pots with twice weekly water changes and screened three times with individual screens having been 7 days apart. Once fish had been screened clear for three times they were returned to breeding stock aquaria or donated to hobbyists.

Statistical Analysis

Efficacy of treatments in all trials was assessed using the following equation:

$$E_t = (L_0 - L_t)/L_0 \text{ for } L_t < L_0, \text{ and}$$

$$\Delta E_t = 0 \text{ for } L_t > L_0.$$

Where $L_0$ = parasite load at start of treatment $L_t$ = parasite load at end of treatment and $E_t$ = efficacy of treatment at time t.

Anderson-Darling Test for Normality and Bartlett's Test for heterogeneity indicated non normal distribution of data and heterogeneity of variance, respectively, in all data sets. Data transformation was unsuccessful, hence, the non-parametric Kruskal-Wallis Test and post hoc Mann-Whitney Tests (with Bonferroni corrections) were used to compare efficacies of treatments. All data were analysed in Minitab vs. 15.

Results

Host Mortality

Host mortalities in Trial 1 were extremely high due to the poor general health of the fish on arrival in Cardiff (Table 1). In Trial 2, allyl disulphide appeared to increase host mortality by 15% compared to the control and Trial 3 resulted in high mortalities when fish were treated with Melafix® and Levamisole (increasing concentration) (Table 1). As yet, results of Trial 3 are inconclusive due to the low number of replicates.

TABLE 1

Table 1. Host mortalities (%) in Trials 1-3.

| Treatment | Trial 1 | Trial 2 | Trial 3 |
|---|---|---|---|
| Mortality control (uninfected fish) | — | 0 | 0 |
| Negative control (infected fish) | 75 | 35 | 33 |
| Melafix ® | 55 | 20 | 66 |
| Pimafix ® | 42 | 10 | 17 |
| Melafix ®/Pimafix ® | 59 | 5 | — |
| Polyaqua ® | 68 | — | — |
| Allyl disulphide | — | 50 | 33 |
| Levamisole (constant concentration) | — | — | 33 |
| Levamisole (increasing concentration) | — | — | 83 |

Trial 1 (Multi-Parasite, Single Fish, Low Dose, 7 Day Treatment)

Melafix appeared to prevent increasing parasite burdens, and the combination treatment Melafix®/Pimafix® reduced the prevalence of infected fish considerably (Table 2).

TABLE 2

Table 2. Mean intensity, prevalence and range of parasite numbers in Trial 1.

| Treatment | Mean Intensity Day 1 | Mean Intensity Day 8 | Prevalence D8 (in %) | Range D8 min | Range D8 max |
|---|---|---|---|---|---|
| Negative control (infected fish, untreated) | 11 | 122.5 | 100 | 33 | 194 |
| Melafix ® | 9.3 | 14.8 | 85.7 | 1 | 38 |
| Pimafix ® | 11.8 | 60.9 | 81.3 | 1 | 190 |
| Melafix ®/Pimafix ® | 7 | 19.8 | 36.4 | 1 | 72 |
| Polyaqua ® | 9.4 | 48.7 | 100 | 5 | 201 |

Trial 2. (single parasite, single fish, low dose, 7 day treatment)

Melafix'® efficacy was highly variable, however, when used in combination Melafix®/Pimafix® was extremely efficient (Kruskal Wallis: H=72.05; DF=5; p<0.001).

Allyl disulphide and Pimafix® were not effective (Table 3).

TABLE 3

Table 3. Results of post hoc Mann Whitney Tests between treatments.

| Treatment | Inf Control | Allyl disulphide | Pimafix ® | Melafix ® |
|---|---|---|---|---|
| Allyl disulphide | NS | | | |
| Pimafix ® | NS | P = 0.0004 | | |
| Melafix ® | P = 0.0014 | P < 0.0001 | NS | |
| Pimafix ®/Melafix ® | P < 0.0001 | P < 0.0001 | P < 0.0001 | NS |

All p-values (adjusted for ties) were compared to P = 0.005 (after Bonferroni corrections).
NS = not significant.

CONCLUSION

Despite not being marketed as anti-helminthic treatments, a combination of Melafix®/Pimafix® was the most effective treatment test in removing *Gyrodactylus turnbulli* infections on guppies. Melafix® alone shows a high variation in efficacy which is undesirable as just one single gyrodactylid is enough to cause a new epidemic, and Pimafix® is not effective. Allyl disulphide is effective only when carefully applied (high dose 10 min exposure, followed by low dose 1 h exposure). This is similar to the application protocol used for levamisole, and could be used as replacement for this treatment, particularly as levamisole is more toxic to the fish. However, allyl disulphide was not effective when applied at a low dose, more comparable to applications used in the aquarium trade. Application of levamisole over 7 days was too toxic to the fish (at 0.15-1.05 mg/l), unless daily water changes were performed, but 0.15 mg/l alone was not effective at removing parasites.

The invention claimed is:

1. A method for reducing the incidence of ornamental fish parasite infestation or removing parasites from ornamental fish comprising administering a composition comprising cajeput and *Pimenta racemosa* to the water in which said ornamental fish are found, wherein the combined amount of cajeput and *Pimenta racemosa* is 0.8 ml to 2 ml per 380 liters of water in which the fish are found, wherein the ratio of cajeput to *Pimenta racemosa* in the combined amount is in the range of 0.5:1 to 1:0.5.

2. The method of claim 1, wherein said cajeput is in the form of an aqueous mixture of cajeput oil and water.

3. The method of claim 1, further comprising the step of administering said composition comprising cajeput and *Pimenta racemosa* to an environment for ornamental fish one time daily.

4. The method of claim 1, wherein said parasite infestation is aquatic helminth.

5. The method of claim 1, wherein said ornamental fish is selected from the group consisting of a guppy, a Koi, a mirror or grass carp, an orfe, or a tench.

6. The method of claim 1, wherein the composition further comprises an emulsifier.

7. The method of claim 6, wherein the emulsifier is present at a concentration of about 0.01% to about 20% by volume.

8. The method of claim 1, wherein the composition further comprises a component selected from the group consisting of antifoams or defoamers, antioxidants, preservatives, coloring agents, and combinations thereof.

9. A method for reducing the incidence of ornamental fish parasite infestation or removing parasites from ornamental fish comprising administering a composition comprising cajeput, *Pimenta racemosa*, and an emulsifier to the water in which said ornamental fish are found, wherein the combined amount of cajeput and *Pimenta racemosa* is about 0.1 ml to about 10 ml per 380 liters of water in which the fish are found, wherein the ratio of cajeput to *Pimenta racemosa* in the combined amount is in the range of 0.5:1 to 1:0.5.

10. The method of claim 9, wherein said cajeput is in the form of an aqueous mixture of cajeput oil and water.

11. The method of claim 9, further comprising the step of administering said composition comprising cajeput and *Pimenta racemosa* to an environment for ornamental fish one time daily.

12. The method of claim 9, wherein said parasite infestation is aquatic helminth.

13. The method of claim 9, wherein said ornamental fish is selected from the group consisting of a guppy, a Koi, a mirror or grass carp, an orfe, or a tench.

14. The method of claim 9, wherein the composition further comprises a component selected from the group consisting of antifoams or defoamers, antioxidants, preservatives, coloring agents, and combinations thereof.

15. The method of claim 9, wherein the emulsifier is present at a concentration of about 0.01% to about 20% by volume.

16. The method of claim 9, wherein the combined amount of cajeput and *Pimenta racemosa* is 0.4 ml to 3 ml per 380 liters of water in which the fish are found.

17. A composition comprising a solution of cajeput, *Pimenta racemosa* extract and an emulsifier, wherein the ratio of cajeput to *Pimenta racemosa* extract in the composition is from 0.5:1 to 1:0.5.

18. The composition of claim 17, wherein the emulsifier is a nonionic emulsifier.

19. The composition of claim 17, further comprising one or more antifoams or defoamers, antioxidants, preservatives, coloring agents or a combination of these.

20. The composition of claim 17, consisting of a solution of cajeput, *Pimenta racemosa*, an emulsifier and a defoamer.

21. An article of commerce comprising a composition comprising a solution of cajeput and *Pimenta racemosa* extract in a ratio of from 0.5:1 to 1:0.5 and instructions for use indicating that the composition should be introduced daily in water in which fish are found at a concentration of from 0.4 mL to 3 mL per 380 Liters of water to reduce the incidence of ornamental fish parasite infestation or to remove parasites from ornamental fish.

* * * * *